(12) United States Patent
Portsmouth et al.

(10) Patent No.: US 11,541,429 B2
(45) Date of Patent: Jan. 3, 2023

(54) GEMSTONE SORTING

(71) Applicant: De Beers UK Ltd, London (GB)

(72) Inventors: Andrew John Portsmouth, Sunninghill (GB); Colin McGuinness, Maidenhead (GB); Nicholas Matthew Davies, Reading (GB); David Fisher, Maidenhead (GB)

(73) Assignee: De Beers UK Ltd, London (GB)

( * ) Notice: Subject to any disclaimer, the term of this patent is extended or adjusted under 35 U.S.C. 154(b) by 263 days.

(21) Appl. No.: 16/471,839

(22) PCT Filed: Dec. 21, 2017

(86) PCT No.: PCT/GB2017/053865
§ 371 (c)(1),
(2) Date: Jun. 20, 2019

(87) PCT Pub. No.: WO2018/115889
PCT Pub. Date: Jun. 28, 2018

(65) Prior Publication Data
US 2020/0094289 A1 Mar. 26, 2020

(30) Foreign Application Priority Data
Dec. 23, 2016 (GB) ...................... 1622077

(51) Int. Cl.
*B07C 5/02* (2006.01)
*B07C 5/342* (2006.01)
(Continued)

(52) U.S. Cl.
CPC .............. *B07C 5/3427* (2013.01); *B07C 5/02* (2013.01); *B07C 5/36* (2013.01); *G01N 21/87* (2013.01); *G01N 33/381* (2013.01)

(58) Field of Classification Search
CPC ........... B07C 5/02; B07C 5/36; B07C 5/3427; G01N 21/87; G01N 33/381
See application file for complete search history.

(56) References Cited

U.S. PATENT DOCUMENTS 2,835,373 A * 5/1958 Bickley ..................... B07C 5/02
198/636
4,784,493 A * 11/1988 Turcheck, Jr. ............ B07C 5/02
198/395
(Continued)

FOREIGN PATENT DOCUMENTS

CA 2890047 A1 6/2021
CN 102166571 A * 8/2011
(Continued)

OTHER PUBLICATIONS

Glass Gemstone Information. Gemdat.org, 2021 [retrieved on Oct. 27, 2021] Retrieved from the Internet: <URL: www.gemdat.org/gem-26411.html> (Year: 2021).*
(Continued)

*Primary Examiner* — Patrick H Mackey
(74) *Attorney, Agent, or Firm* — Renner, Otto, Boisselle & Sklar, LLP (57) ABSTRACT

There is disclosed an apparatus and method for sorting gemstones from a batch of gemstones. The apparatus comprises one or more measurement locations, each comprising at least one measurement device configured to measure one or more properties of a gemstone. A continuously moveable surface supports the gemstones thereon and transports the gemstones to the one or more measurement locations. A separation device separates the gemstones from one another as they are transported on the moveable surface to the one or more measurement locations. A location trigger at a sensor location comprises a sensor for identifying when the gemstone passes through the sensor location. A controller
(Continued)

receives a signal from the location trigger, records the position of the moveable surface when the signal is received, and tracks the subsequent location of the gemstone by monitoring the movement of the moveable surface such that a measurement of the one or more properties of each gemstone can be correlated with a location of the respective gemstone on the moveable surface. Specific markers in the luminescence properties of the gemstone may be used to identify properties of the stone.

26 Claims, 8 Drawing Sheets

(51) Int. Cl.
   *B07C 5/36* (2006.01)
   *G01N 21/87* (2006.01)
   *G01N 33/38* (2006.01)

(56) References Cited

U.S. PATENT DOCUMENTS

| | | | | |
|---|---|---|---|---|
| 5,135,113 | A * | 8/1992 | Mayer | B07C 5/02 209/931 |
| 5,193,685 | A | 3/1993 | Trevithick | |
| 5,505,313 | A * | 4/1996 | Smith | G01N 21/87 209/579 |
| 5,894,938 | A * | 4/1999 | Ichise | B07C 5/02 209/579 |
| 6,879,389 | B2 * | 4/2005 | Meyer | B07C 5/02 209/557 |
| 7,126,351 | B2 * | 10/2006 | Claus | G01N 33/381 324/687 |
| 9,008,832 | B2 | 4/2015 | Lo | |
| 9,618,443 | B2 * | 4/2017 | Smith | G01N 21/87 |
| 9,731,328 | B2 * | 8/2017 | DeFillipi | B07C 5/342 |
| 11,020,771 | B2 * | 6/2021 | Smith | B07C 5/3425 |
| 2002/0112996 | A1 | 8/2002 | Linge et al. | |
| 2014/0119613 | A1 | 5/2014 | D'Gama et al. | |

FOREIGN PATENT DOCUMENTS

| | | | | |
|---|---|---|---|---|
| CN | 102166571 | A | 8/2011 | |
| CN | 104169011 | A | 7/2017 | |
| DE | 2148582 | B2 | 2/1974 | |
| DE | 19949656 | A1 * | 4/2001 | B07C 5/3425 |
| DE | 19949656 | A1 | 4/2001 | |
| EP | 1795888 | A1 | 8/2017 | |
| ES | 2219483 | T3 | 12/2004 | |
| GB | 1560446 | A | 2/1980 | |
| GB | 2500259 | A * | 9/2013 | G01N 21/13 |
| GB | 2500259 | A | 9/2013 | |
| GB | 2552138 | A | 1/2018 | |
| GB | 2554467 | A | 4/2018 | |
| RU | 2016672 | C1 | 7/1994 | |
| RU | 2 424 859 | C1 | 7/2011 | |
| WO | 2014/067932 | A1 | 5/2014 | |
| WO | 2015183947 | A1 | 12/2015 | |

OTHER PUBLICATIONS

International Preliminary Report on Patentability (IPRP) for corresponding App. No. PCT/GB2017/053865, dated Jun. 25, 2019.
International Search Report and Written Opinion for corresponding Application No. PCT/GB2017/053865, dated Mar. 14, 2018.
Search Report for corresponding Application No. GB 1622077.4, dated May 5, 2017.

* cited by examiner

Figure 1

PRIOR ART

GEMSTONE SORTING

TECHNICAL FIELD

The present invention relates to a method and an apparatus for sorting gemstones. In particular, although not exclusively, the invention relates to a method and an apparatus for sorting diamonds.

BACKGROUND

Natural diamonds are stones from nature, consisting exclusively of diamond formed by geological processes over long periods of time. Synthetic diamonds are man-made stones manufactured by industrial processes, such as HPHT (high pressure high temperature) and CVD (chemical vapour deposition).

Synthetic diamonds have a wide range of industrial applications, but currently form only a small percentage of the gemstone industry, and do not attract the high values associated with natural diamonds of similar colour and quality. Synthetic diamonds may be relatively easy to distinguish from natural diamonds when in an unpolished state, however, once polished and cut into a gemstone, identification that a stone is synthetic may be more difficult.

Advanced screening instruments, such as the DiamondSure™ and DiamondView™, may be used to test whether a stone is natural or synthetic. Typically, such screening involves measuring the way in which light is absorbed by or emitted from a diamond.

Before screening commences it is usually necessary for the stone being tested to be placed "table-down" in a precise location on the measurement surface or holder. In this context, the "table" is the largest central facet of the crown (the top half of the stone when mounted).

In addition to screening larger, individual stones, it is also necessary to screen large numbers of smaller diamonds, including stones sometimes known as melee. Melee is a term of the trade that does not have a well-defined size range, but can be considered in practice to refer to stones smaller than about 0.2 carats (20 points), and usually (but not necessarily) larger than about 0.01 or 0.02 carats. Due to their small size, melee stones are typically sold in parcels or lots. Since one parcel may contain hundreds of stones, it is possible for synthetic diamonds and non-diamond material to be mixed in with natural stones.

Screening of melee diamonds can potentially be extremely time consuming, since each stone must be tested individually and therefore placed in the correct orientation individually. WO 2012/146913 discloses an apparatus for orientating gemstones, in which discrete gemstones are provided on a travelling path which has a pair of opposed oscillating walls. These walls urge the gemstones into their most stable orientation (i.e. table-down) as they progress along the path. Once in this orientation, individual stones may be lifted from the travelling path by a vacuum wand and transported to a test station.

Figure 1:
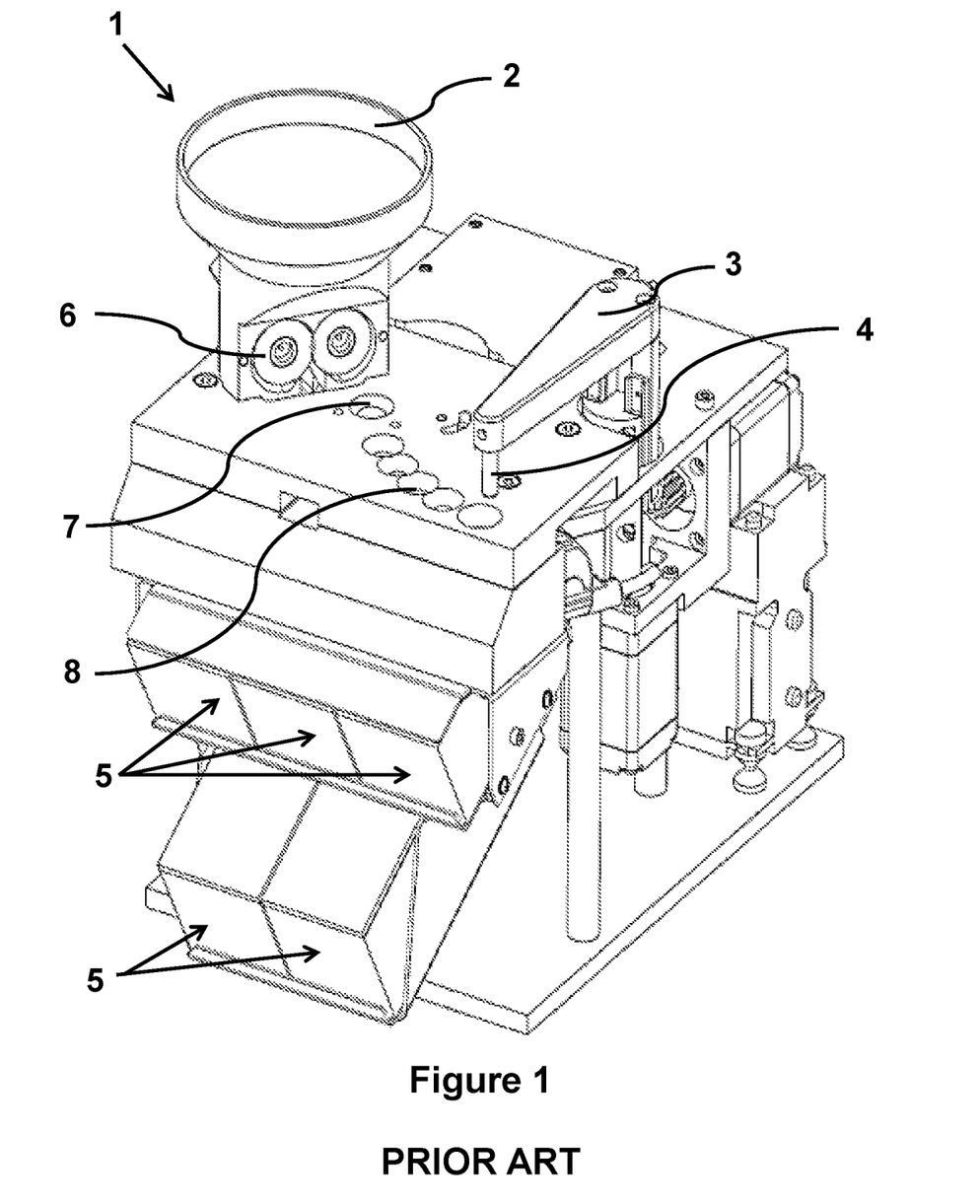
FIG. 1 is a perspective view of a known apparatus for orientating gemstones.
Figure 2:
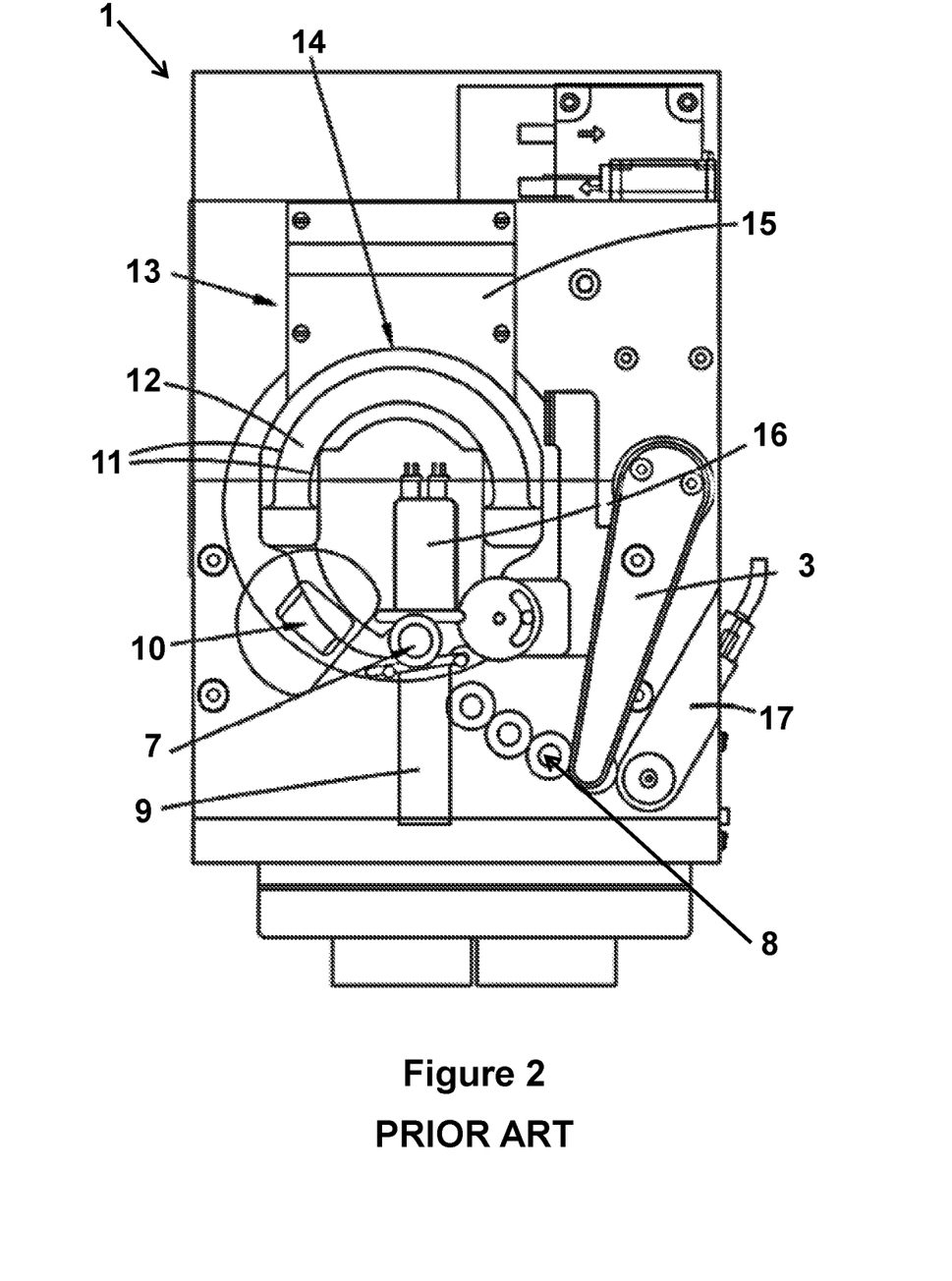
FIG. 2 is a plan view of the apparatus of FIG. 1, with components removed for clarity.

FIG. 1 is a view of the apparatus 1 described in WO 2012/146913 for orientating gemstones. The melee stones are poured into a hopper 2 and pass through a pair of rollers 6. The speed of the rollers 6 is configured to separate out the stones so they pass through one at a time. The stones are then directed onto a rotating disc 10, as shown in FIG. 2. The disc 10 rotates clockwise and provides a circular travelling path, passing the stones through an agitator 13. The agitator 13 comprises a pair of opposed parallel vertical walls 11 which form a semi-circular channel 12. The walls 11 are connected to an oscillator 15 which oscillates the walls with sufficient magnitude and frequency that they collide with the stones on the travelling path. The centre of the pair of walls 14 oscillates along the radius of the rotating disc 10.

The impact level of the walls 11 is chosen such that it is enough to knock a stone off its pavilion facet, but not to knock a stone off its most stable table facet. Eventually, the stones land table-down and are aligned by the time they reach a handling area 7. An orientation checking device 9 checks that each stone is table-down, by recording a side view silhouette image of the stone with a camera 16. If the stone is found to be correctly orientated, it is collected by the handler, comprising a swinging arm 3 and a vacuum wand 4, and transported to a synthetic detection device 17. If the stone is found to be incorrectly orientated, it will be transported back to the oscillating channel 12 to be re-orientated. This process continues until all stones in the melee have been orientated, tested and dispensed into an appropriate collection bin 5 via chutes 8.

While the apparatus of FIG. 1 speeds up the orientation and testing process, it is still necessary to halt the rotation of the disc 10 each time an oriented stone is ready to be picked up by the vacuum wand 4. Moreover, conventional testing devices and methods often fail to conclusively identify a stone as natural or synthetic. Where a conclusive identification is not possible, stones must be "referred" for further testing. Further testing typically requires the use of more complex methods such as photoluminescence or Raman spectroscopy and/or one or more different devices. For very small gemstones, further testing may not be economically viable. WO 2015/024979 describes one system which attempts to address this problem by distinguishing between diamond and non-diamond material on a rotating glass disc using Raman spectroscopy and subsequently carrying out measurements of UV transmission intensity on stones passed as containing diamond material.

SUMMARY

In accordance with one aspect of the present invention there is provided an apparatus for sorting gemstones from a batch of gemstones. The apparatus comprises one or more measurement locations, each comprising at least one measurement device configured to measure one or more properties of a gemstone. A continuously moveable surface supports the gemstones thereon and transports the gemstones to the one or more measurement locations. A separation device separates the gemstones from one another as they are transported on the moveable surface to the one or more measurement locations. A location trigger at a sensor location comprises a sensor for identifying when the gemstone passes through the sensor location. A controller receives a signal from the location trigger, records the position of the moveable surface when the signal is received, and tracks the subsequent location of the gemstone by monitoring the movement of the moveable surface such that a measurement of the one or more properties of each gemstone can be correlated with a location of the respective gemstone on the moveable surface. Specific markers in the luminescence properties of the gemstone may be used to identify properties of the stone.

In accordance with another aspect of the present invention there is provided a method of sorting gemstones from a batch of gemstones. The method comprising the steps of: transporting gemstones to one or more measurement locations on a continuously moveable surface; separating the gemstones from one another as they are transported on the moveable surface to the one or more measurement locations; after the gemstones have been separated, identifying each moment that a gemstone passes a sensor location, associating that gemstone with the position of the moveable surface at that moment, and tracking the subsequent location of the gemstone by monitoring the movement of the moveable surface; measuring one or more properties of a gemstone at the one or more measurement locations; and correlating each measurement of the one or more properties of each gemstone with the location of the respective gemstone on the moveable surface.

The one or more properties may comprises one or more specific markers in the luminescence properties of the gemstone. These markers may include the wavelength and decay time of the luminescence. Particular combinations of markers may provide indications as to whether or not the stone contains diamond material and, if so, whether it is natural or synthetic or requires further testing.

Further aspects and preferred features are set out in claim 2 et seq.

DETAILED DESCRIPTION

An apparatus 101 for sorting gemstones, such as diamonds, from a batch of gemstones, will now be described with reference to FIGS. 3 to 7. The gemstones to be sorted will typically comprise polished stones, both brilliant and fancy cut. A method of sorting gemstones from a batch will be described with reference to FIG. 8.

The apparatus 101 comprises one or more measurement locations 110a, 110b, each comprising at least one measurement device configured to measure one or more properties of a gemstone, and a moveable surface 103 for supporting the gemstones thereon and for transporting the gemstones to the one or more measurement locations 110a, 110b. The apparatus 101 further comprises a separation device 107, 108 for separating the gemstones from one another as they are transported on the moveable surface 103 to the one or more measurement locations 110a, 110b. Once the gemstones have been separated, each passes through a location trigger such as a laser curtain 109. The position of that stone on the movable surface 103 is then known, and the subsequent location of the stone can be tracked by monitoring the movement of the surface 103. This enables measurements at the one or more measurement locations 110a, 110b to be correlated with the known locations of the gemstones on the moving surface 103.

In the embodiment of FIGS. 3 to 7, the moveable surface comprises a rotatable disc 103 having a substantially flat upper surface on which gemstones can be transported. The disc 103 is rotated by a motor (not shown here) at a rotational speed of approximately between 9 degrees/second and 13.5 degrees/second, depending on the size of the gemstones to be transported. The rotational speed of the disc 103 can be controlled via a controller, optionally including a screen 117.

In the illustrated example of FIGS. 3 to 7, the surface of the rotatable disc 103 is manufactured to be flat, within a tolerance of 50 microns. The disc 103 is also hard black anodised so that it is hardwearing and to allow for measurements at the one or more measurements locations to be carried out in a substantially dark environment, as will be further discussed below. To this end, the disc 103 is also provided with a cover 104 which defines viewing ports through which gemstones being transported upon the disc 103 can be viewed.

Figure 3:
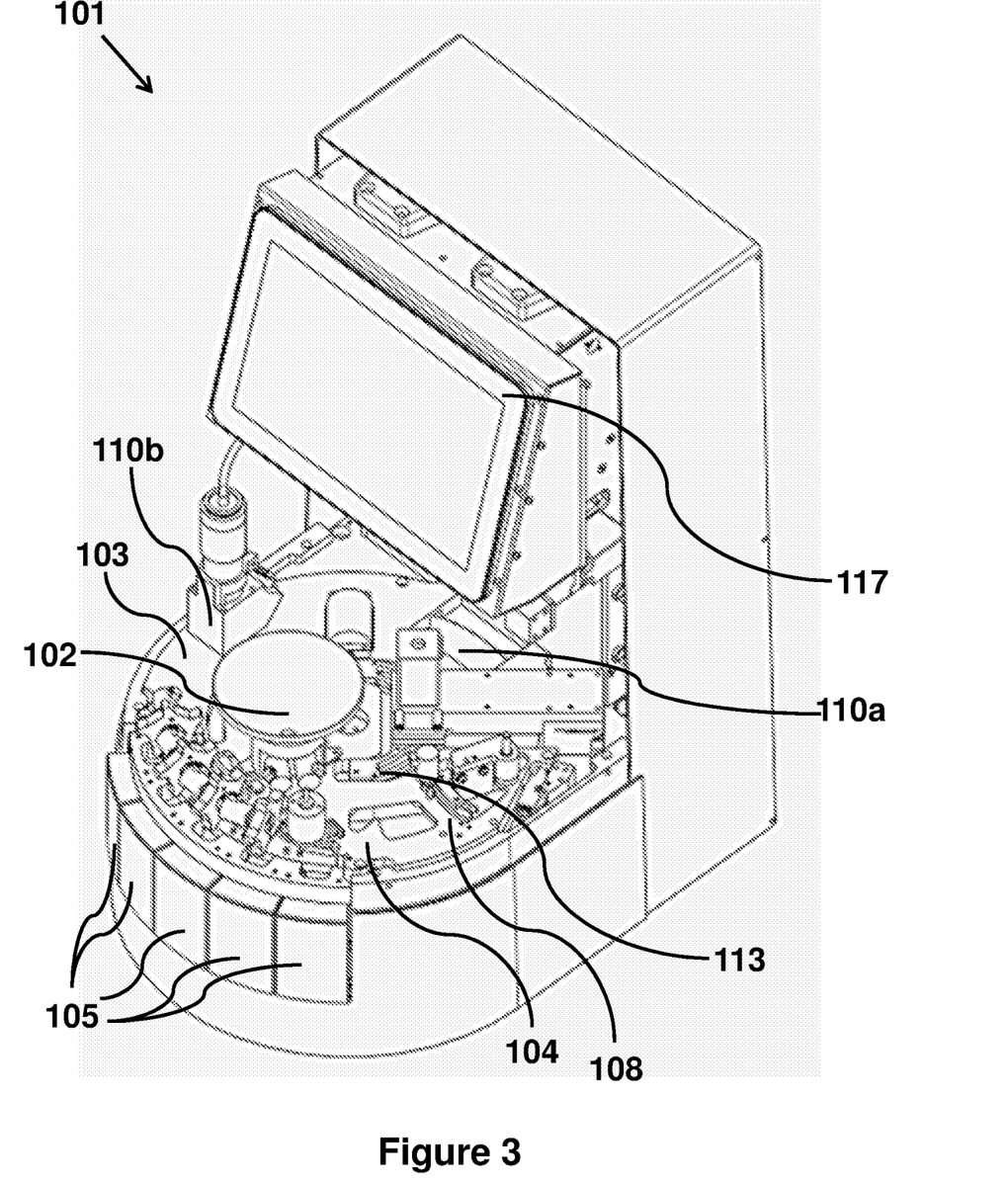
FIG. 3 is a perspective view of an apparatus for orientating gemstones according to the present invention.

As best shown in FIG. 3, the apparatus 101 comprises a hopper 102 for receiving and delivering a batch of gemstones onto the surface of the rotatable disc 103, near the centre of the disc 103. The hopper 102 may be a hopper of the type described above with reference to FIGS. 1 and 2. The hopper 102 comprises two counter-turning foam rollers (not shown here) which are used to control the flow of gemstones onto the rotatable disc 103. The speed of the rollers may be controlled via the controller 117 and can be varied according to the size and shape of gemstones being sorted. In this example, the hopper 102 has a minimum capacity of around 500 carats and is typically suitable for gemstones of between around 0.3 points to 30 points.

Figure 4:
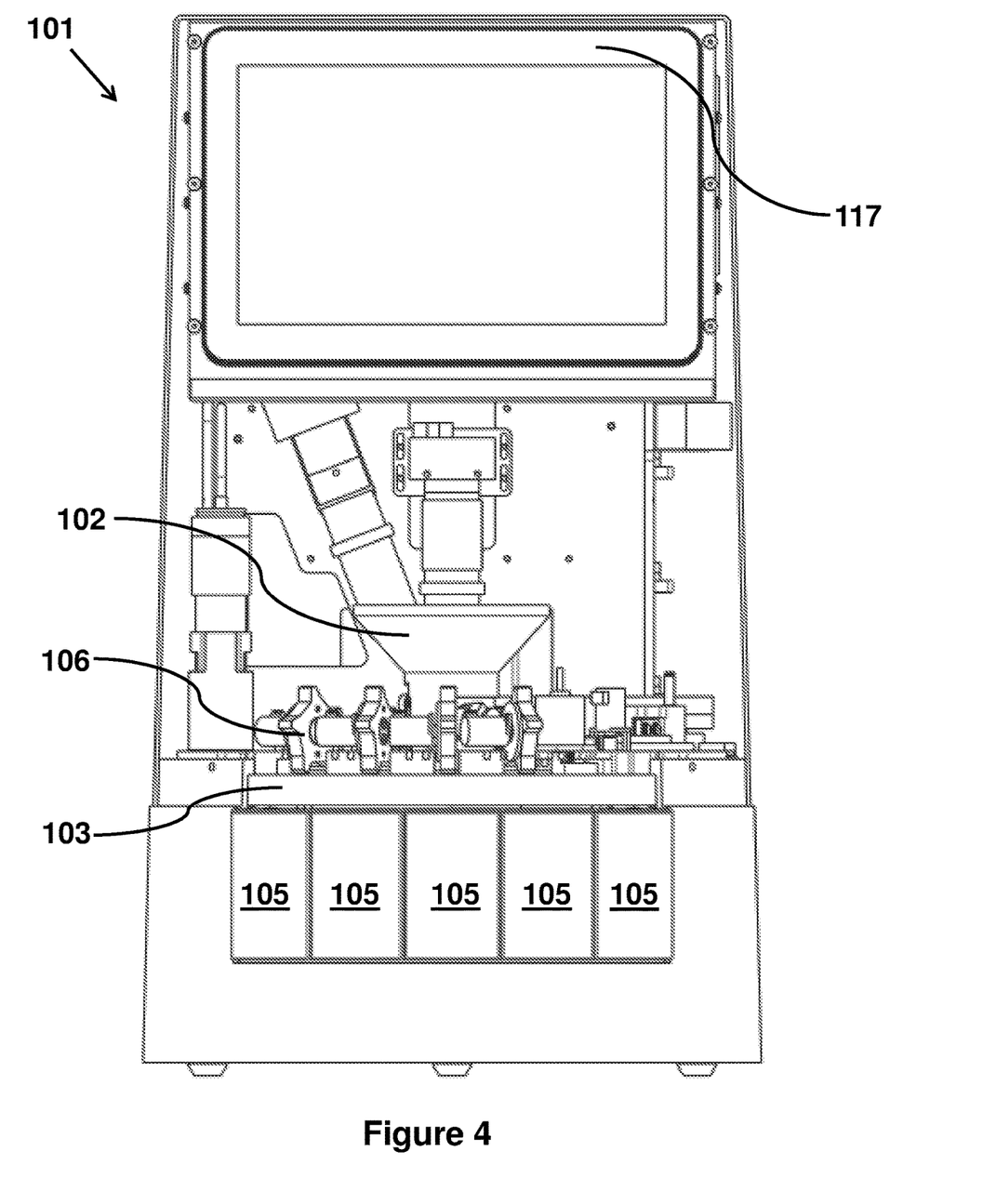
FIG. 4 is a front view of the apparatus of FIG. 3.
Figure 5:
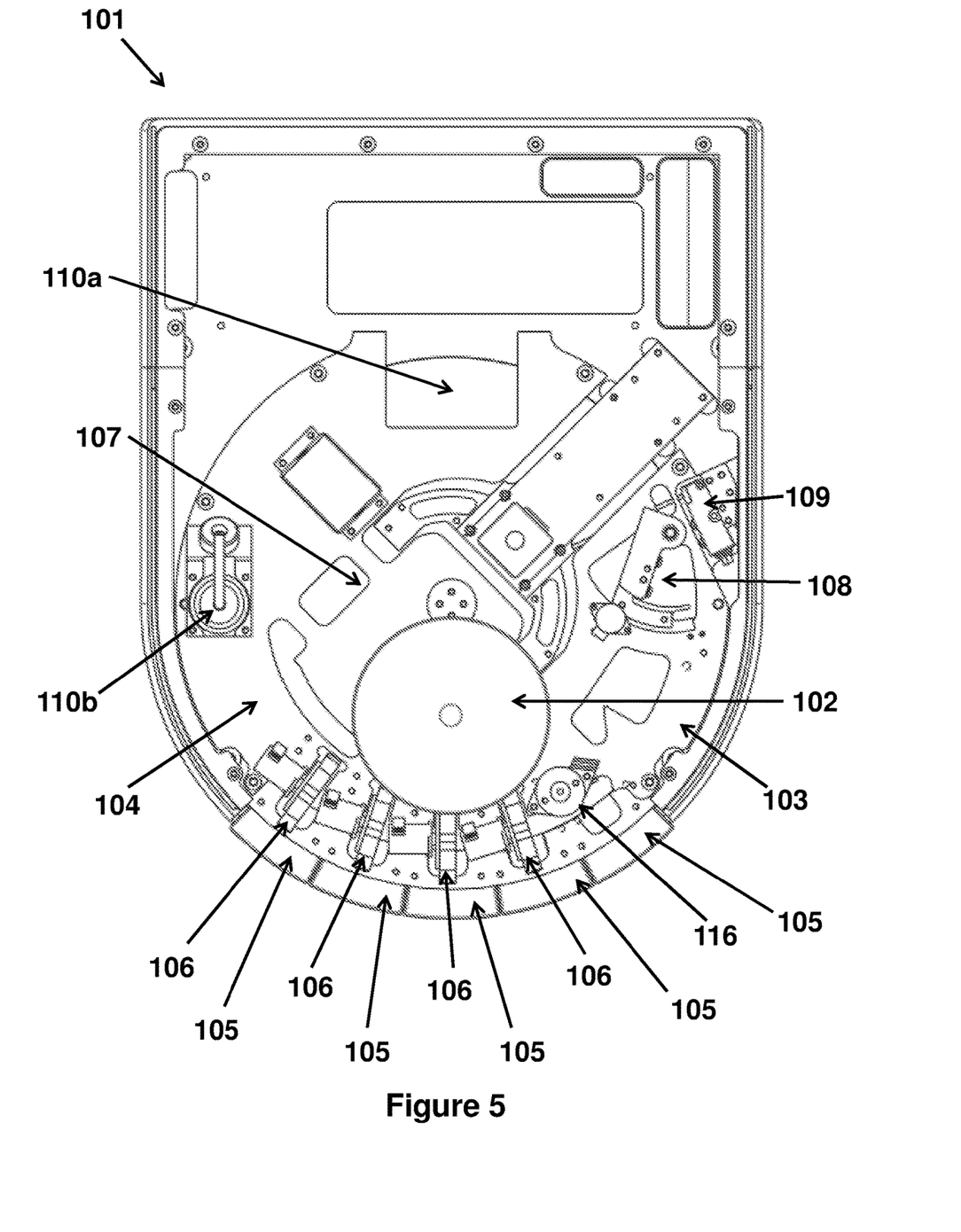
FIG. 5 is a top down view of the apparatus of FIG. 3.
Figure 6:
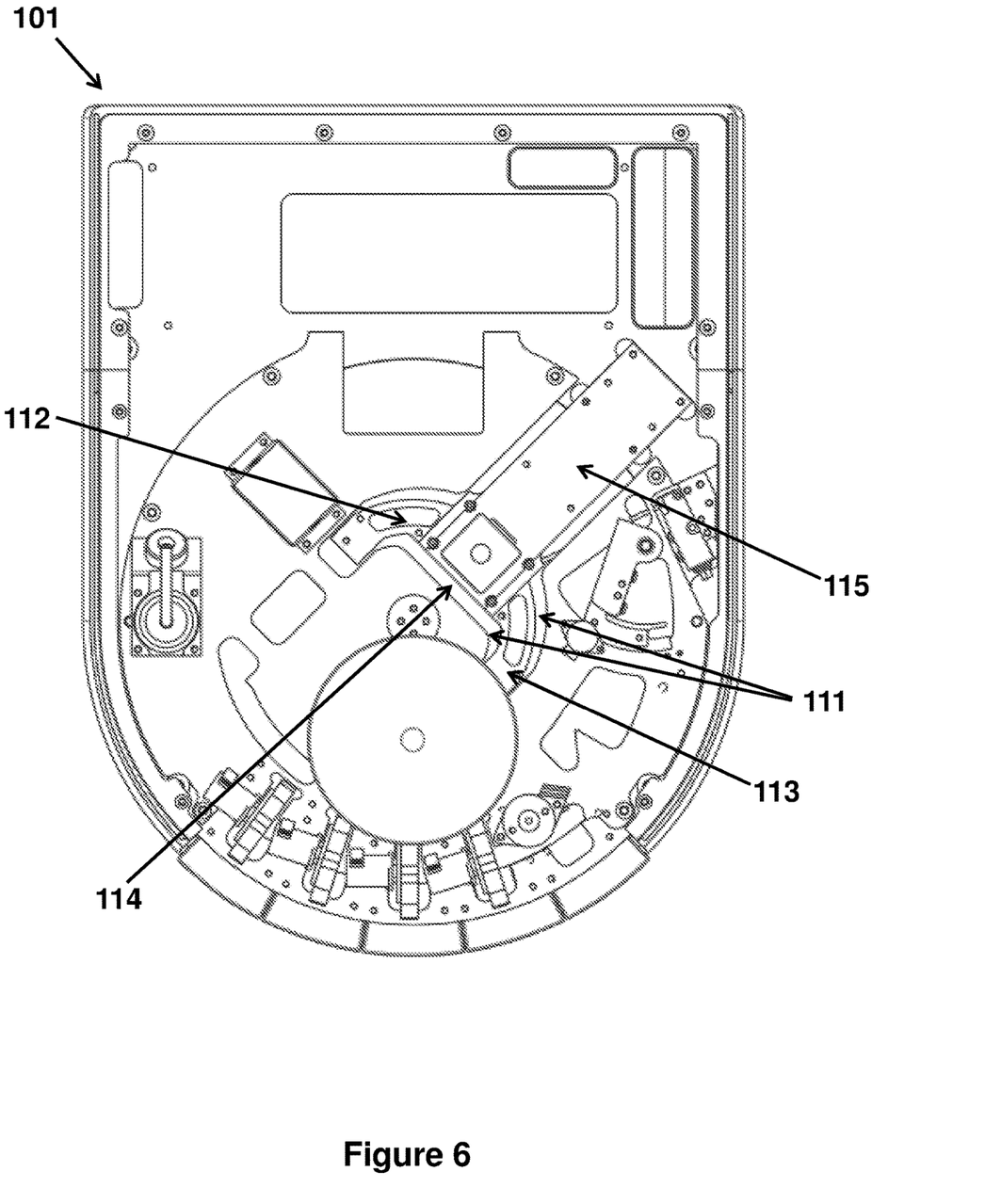
FIG. 6 is a further top down view of the apparatus of FIG. 3, illustrating an orientation device.

In the embodiment of FIGS. 3 to 7 and as best shown in FIG. 5, the apparatus 101 further comprises an orientation device for orienting the gemstones as they are transported on a central portion of the rotatable disc 103, such that the gemstones are oriented into their most stable configuration prior to being separated from one another. In this example, the orientation device comprises an agitator 113 of the type described with reference to FIGS. 1 and 2 above, although without the vacuum wand. The agitator 113 comprises a pair of opposed parallel vertical walls 111 which form a substantially semi-circular channel 112, into which the gemstones are guided by the rotatable disc 103.

The walls 111 are oscillated by an oscillator 115 such that a central portion 114 of the pair of walls 111 oscillates along the radius of the rotatable disc 103 i.e. generally transverse to the direction of travel of the gemstones. It will be understood that relative transverse movement of the pair of walls 111 may be minimal at the entry and exit portions of the semi-circular channel 112.

The walls 111 are oscillated with sufficient magnitude and frequency that they collide with the gemstones that are present on the surface of the rotatable disc 103, knocking them into their most stable configuration i.e. their position of lowest potential energy. For the vast majority of cut gemstones, the most stable configuration will be table facet down. The impact level of the walls 111 is selected so that once a gemstone has landed on its most stable facet it will not be knocked over again and will remain in its most stable configuration. In other words, the impact level of the agitator 113 is carefully selected so that it is sufficient to knock a gemstone off its pavilion facet, for example, but not sufficient to knock a gemstone off its table facet.

The length of the oscillating walls 111 is chosen so that all of the gemstones will have been orientated into their most stable configuration by the time they leave the agitator 113. Gemstones which have been oriented into their most stable configuration are easier to separate, measure and dispense as they handle more predictably.

The apparatus 101 of this embodiment comprises a separation device 107, 108 for separating the gemstones from one another as they are transported on the rotatable disc 103 to the one or more measurement locations 110a, 110b. In the embodiment shown in FIGS. 3 to 7, the separation device comprises a series of fixed cams 107 and a moveable cam 108. The gemstones come into contact with the cams 107 as the disc 103 rotates. The fixed cams 107 are inclined to the direction of travel of the horizontal surface so that the gemstones are pushed towards an outer region of the disc 103, which is moving faster than the central region of the disc 103. This thus increases the separation between the stones. Successive cam 107 surfaces may be inclined to the direction of travel of the horizontal surface of the rotatable disc 103 by successively smaller angles, and/or the cams 107 may include bent surfaces so as to optimise the rate at which the stones are moved laterally across the moving surface. In this example, there are three fixed cams 107, but it will be appreciated that fewer or additional cams 107 may be employed, as required.

Since each cam 107 pushes the gemstones successively further away from the central region of the rotatable disc 103, this naturally causes the gemstones to separate one from another as their average angular position with respect to the disc 103 is maintained while their distance from the centre of the rotatable disc 103 increases.

The embodiment of FIGS. 3 to 7 further includes a moveable cam 108, with which the gemstones come into contact after they have passed the fixed cams 107. The angle of the moveable cam 108 surface can be adjusted in accordance with the size and shape of gemstone to be sorted. The moveable cam 108 is used to provide the final separation between the gemstones. In this way, once the gemstones have passed the moveable cam 108, a stream of separated gemstones is provided on the surface of the rotatable disc 103. Although only one moveable cam 108 is provided in this example, it will be appreciated that further moveable cams may be provided as required. Additionally, the sequence of fixed and moveable cams may be varied.

As shown in FIG. 5, the apparatus 101 also comprises a location trigger 109. This is located at a sensor location on the disc 103 that the stones pass through after they have been separated, such that they need not make contact with any other item as they continue to travel on the disc 103. In this embodiment, the location trigger comprises a sensor 109, for example a laser curtain, at the sensor location. The controller 117 is configured to receive a signal from the sensor every time a gemstone passes the sensor. The passage of that gemstone through the sensor is correlated with the angular position of the disc 103 at that moment, and the location of each gemstone can subsequently by tracked by knowledge of the angular position of the disc 103.

The apparatus 101 further comprises one or more measurement locations 110a, 110b, each comprising at least one measurement device configured to measure one or more properties of the gemstones. In the embodiment shown in FIGS. 3 to 7, there are two measurement locations 110a, 110b, as will be described in more detail below. Each measurement location 110a.110b comprises a measurement device or cell (not shown here). Separated gemstones pass through the measurement locations 110a, 110b one at a time, as the disc 103 rotates. Each measurement device measures a property of an individual gemstone as the gemstone moves past i.e. the rotatable disc 103 does not stop when the gemstones arrive at the measurement locations 110a, 110b and all measurements are performed upon moving gemstones. This means that the disc 103 can rotate continuously and the correlation of the stones' position with the angular position of the disc 103 can be relied on. Measurements of the gemstones' properties are transmitted from the measurement devices to the controller 117. Further details of the measurements are detailed below.

The apparatus 101 further comprises a plurality of dispense locations, which in the example shown in FIGS. 3, 4 and 5 comprise collection bins 105. There are five collection bins 105 in this example, although it will be appreciated that the number of bins 105 may be reduced or increased as required. Associated with each collection bin 105 is a dispensing mechanism 106, such as a push bar or a spiked foam wheel, operated via a solenoid 116 and configured to push a gemstone off the outer surface of the rotatable disc 103 and cause the gemstone to be dispensed into an associated collection bin 105. The five collection bins 105 illustrated in FIGS. 3, 4 and 5 may be designated as follows:

1. non-diamond (for gemstones which consist of simulants e.g. cubic zirconia)
2. synthetic (for synthetic diamonds, such as those grown by CVD or HPHT)
3. pass (for natural diamonds)
4. refer (for gemstones whose properties have not been conclusively determined)
5. purge (for use when it is desired to quickly empty the apparatus of gemstones).

It will be appreciated that the above sequence of collection bins 105 is provided by way of example only and other designations and sequences may be envisaged.

Since the time at which a specific gemstone passes the sensor location and the rotational speed of the disc 103 are known, the controller 117 can accurately predict when the specific gemstone will pass the one or more measurement locations 110a, 110b. A measurement of one or more properties of the specific gemstone received by the controller 117 can therefore be correlated by the controller 117 with a location of the specific gemstone on the rotatable disc 103. The controller 117 can determine whether, for example, a specific gemstone is natural diamond, synthetic diamond or non-diamond, based upon the received measurements. When the specific gemstone arrives at a location adjacent the appropriate collection bin 105, the controller 117 activates the appropriate dispensing mechanism 106 to dispense the gemstone into the correct bin 105.

The apparatus 101 of FIGS. 3 to 7 will now be described in use. A batch of gemstones is deposited into the hopper 102 and gemstones are individually delivered, via the foam rollers of the hopper 102, onto the surface of an inner region of the rotating disc 103. As the disc 103 rotates, the gemstones are introduced into the semi-circular channel 112 of the agitator 113, where they are oriented table-down. Upon leaving the agitator 113, the gemstones are brought by the rotating disc 103 into contact with the series of fixed cam surfaces 107 and the moveable cam surface 108, and are deflected towards an outer region of the rotatable disc 103, becoming separated from one another in the process. Thus, a separated stream of gemstones is transported by the rotatable disc 103 to the sensor location, where individual gemstones pass the sensor (laser curtain) 109 one at a time.

The separated gemstones are then transported by the rotatable disc 103 through two successive measurement locations 110a, 110b, such that individual and different measurements are obtained of each gemstone at each location 110a, 110b. These measurements are transmitted to the controller 117 and associated with the gemstones to which they relate. The controller 117 tracks the accurate location of each measured gemstone, and activates the appropriate dispensing mechanism 106 to dispense the measured gemstone into the appropriate collection bin 105. The appropriate bin 105 is determined by the controller 117, based upon the measured properties of the gemstone.

Figure 7:
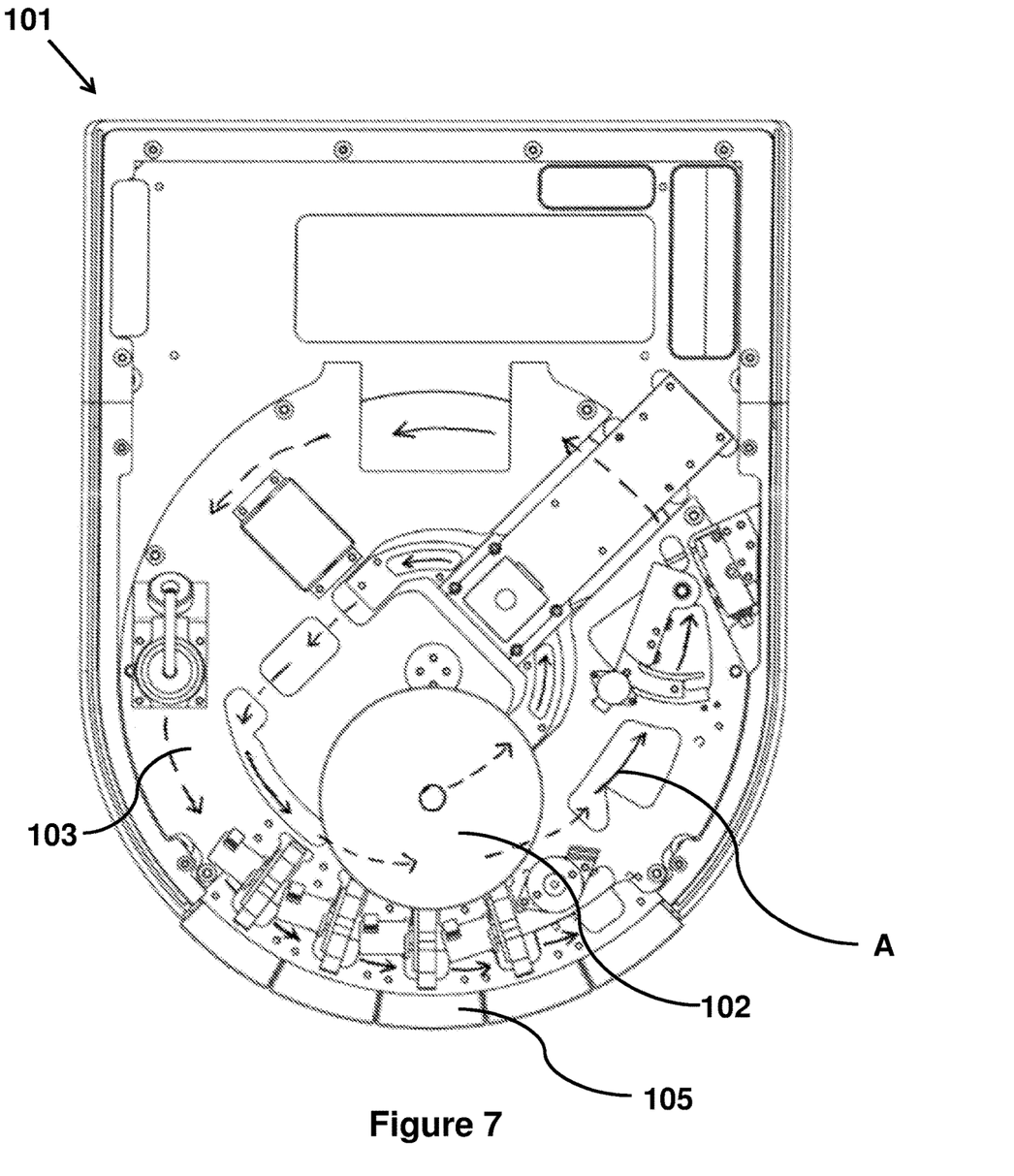
FIG. 7 is a top down view of the apparatus of FIG. 3, illustrating a direction of travel of a batch of gemstones.

Hence, as illustrated in FIG. 7, a gemstone deposited by the hopper 102 onto an inner region of the rotating disc 103 follows a travelling path substantially as indicated by arrows A and eventually arrives at an outermost region of the disc 103, where it is dispensed into a collection bin 105. It will be appreciated that, since the batch of gemstones is deposited onto the rotatable disc 103 gradually, the orientation, separation, measurement and dispensing of gemstones from the batch may take place simultaneously. In other words, the first gemstones from the batch to be deposited onto the disc 103 may be being dispensed as subsequent gemstones from the same batch are being oriented, separated or measured. In this way, the entire batch of gemstones may be sorted without the need to stop the rotation of the disc 103, and hence the apparatus 101 of FIGS. 3 to 7 is capable of sorting a batch of gemstones into appropriate collection bins 105 at an approximate speed of at least 3,600 gemstones per hour.

It will be noted that, in a situation where a gemstone is determined by the controller 117 to have been incorrectly measured, or not measured at all, this gemstone may not be dispensed into a bin 105 but may instead remain upon the surface of the rotating disc 103. The gemstone may then be "recycled" by being deflected back to an appropriate inner region of the disc 103, so that it can pass the sensor and measurement locations 110a, 110b again.

As described above, the apparatus 101 of FIGS. 3 to 7 comprises two measurement locations 110a, 110b, each comprising at least one measurement device configured to measure one or more properties of a gemstone. Separated gemstones are transported through the measurement locations 110a, 110b on the moving surface of the rotatable disc 103 one at a time. As discussed above, measurements at the measurements locations 110a, 110b are carried out in a substantially dark environment.

Since the gemstones on the disc 103 do not come into contact with any other part of the apparatus after passing the sensor location, the location of each gemstone is accurately known by the controller 117 and the controller 117 can therefore accurately determine when a specific gemstone will arrive at each of the two measurement locations 110a, 110b. Measurements taken at each measurement location 110a, 110b can therefore be associated by the controller 117 with the specific gemstone to which they relate. Moreover, as the measurements taken do not require physical contact with the gemstones, the controller 117 can also accurately determine when a specific gemstone will arrive at each of the collection bins 105.

In this embodiment, the first measurement location 110a comprises a luminescence measurement cell. The luminescence measurement cell comprises a source of electromagnetic radiation at wavelengths of substantially 225 nanometres (nm) or less (i.e. an ultraviolet or UV lamp) for exciting a gemstone, and a light detection device or camera for capturing any visible light emitted by the gemstone upon excitation by the electromagnetic radiation.

The operation of the UV lamp and the camera is synchronised by the controller 117, taking into account any offset value applicable to the camera. The lamp used in this example is a microsecond xenon spark lamp, such as a Perkin Elmer FX-4402, filtered to provide above diamond band-gap excitation at wavelengths of less than 225 nm.

The camera in this example makes use of a complementary metal oxide semiconductor (CMOS) sensor, such as the Sony IMX174. Since the position of a specific gemstone upon the rotatable disc 103 is known by the controller 117, the excitation pulse and camera operation can be triggered to coincide with the arrival of a specific gemstone at the excitation and detection areas of the luminescence measurement cell 110a.

The camera can be configured with a delay by the controller system 117 so that the camera is able to only capture visible light during a time window which begins after the excitation pulse produced by the lamp has ended. Thus, the camera can capture phosphorescence as well as fluorescence. Since, in the vast majority of cases, the fluorescence decay is on time-scales shorter than that of the excitation source used here, it will be understood that fluorescence is a type of luminescence characterised as only being produced during ultraviolet excitation of the gemstone. Consequently, any fluorescence produced during excitation will decay very rapidly once the excitation is terminated. Phosphorescence on the other hand is a type of luminescence that remains once the excitation is removed, but subsequently decays away over a longer timescale. Phosphorescence can persist for some time after the excitation is terminated, or can decay within milliseconds of the end of the excitation pulse. The process of delaying capture of visible light until the excitation pulse has ended and any fluorescence has decayed ensures that the fluorescence is "gated out" and does not obscure any phosphorescence emitted after the end of the excitation pulse. The end of the time window for capturing visible light emitted by a gemstone may also be carefully selected to choose the decay time of the fluorescence and/or phosphorescence captured. In this way, the apparatus can capture visible light emissions which might otherwise be missed.

A method of determining whether a gemstone is natural or synthetic by observing certain specific markers in the luminescence properties of the gemstone will now be described. The method may comprise irradiating the gemstone with multiple excitation pulses of electromagnetic radiation, and during and/or following each excitation pulse, detecting light emitted by the diamond in at least one time window having a predetermined time relationship relative to the excitation pulse so as to obtain luminescence data. The or each time window is chosen to include luminescence having a decay time characteristic of one or more of the markers. The luminescence data associated with all of the pulses may be combined and then analysed in order to establish the presence or absence of the one or more markers. These pulses and detections all take place as the stone passes through the measurement location 110a.

One of the markers may be a blue fast phosphorescence marker comprising luminescence in a wavelength band peaking at about 450 nm and a decay time of less than about 80 milliseconds (ms). Testing for this may involve testing, in a time window opening at or after the end of the excitation pulse and ending about 80 milliseconds after the end of the associated excitation pulse, for a luminescence band peaking at about 450 nm. The presence of the blue fast phosphorescence marker may be an indicator that the diamond is a natural type IIa or Ia diamond.

One of the markers may be a turquoise slow phosphorescence marker comprising luminescence having a wavelength peaking at about 480 nm and a decay time greater than 80 milliseconds. Testing for this may comprise testing, in a time window opening about 80 milliseconds after the end of the associated excitation pulse, for a luminescence band centred around 480 nm. The time window may close about 500 ms after the end of the associated excitation pulse, especially if multiple excitation pulses are used. The presence of the turquoise slow phosphorescence marker may be an indicator that the diamond is a type IIb diamond.

One of the markers may be a green slow phosphorescence marker comprising luminescence having a wavelength between about 530 nm and about 550 nm and a decay time greater than 80 milliseconds. Testing for this marker may involve testing, in a time window opening about 80 milliseconds after the end of the associated excitation pulse, for a luminescence band between about 530 nm and about 550 nm. Again, the time window may optionally close about 500 ms after the end of the associated excitation pulse. The presence of the green slow phosphorescence marker may be an indicator that the diamond should be referred for further testing.

One of the markers may be an "absence" marker where negligible luminescence is detected after the excitation pulse has ended. The presence of such a marker is an indicator that the diamond should be referred for further testing.

One of the markers may be an orange long lived fluorescence marker comprising luminescence having a wavelength between about 535 nm and about 600 nm and a decay time less than 1 millisecond. The presence of the orange long lived fluorescence marker may be an indicator that the diamond should be referred for further testing.

One of the markers may be a red phosphorescence marker comprising luminescence having a wavelength between about 575 nm and about 690 nm and a decay time greater than 1 millisecond. The presence of the red phosphorescence marker may be an indicator that the diamond should be referred for further testing.

One of the markers may be a weak green fluorescence marker having a wavelength of about 510 nm. Testing for the weak green fluorescence marker may comprise testing in a time window synchronised with an excitation pulse, since fluorescence is only produced during excitation of the gemstone and decays very rapidly once excitation is terminated. As previously discussed, the end of the time window will be carefully selected to coincide with the end of the pulse, so that any phosphorescence emitted after excitation of the gemstone has terminated, which might otherwise obscure the detection of weak fluorescence, will be "gated out". The presence of the weak green fluorescence marker may be an indicator that the diamond should be referred for further testing.

It will be appreciated from the above that the measurement of fluorescence and/or phosphorescence and the presence of certain markers may enable a particular gemstone to be identified by the controller as natural type IIa, Ia or IIb diamond. However, the presence of a green slow phosphorescence marker or an "absence" marker, for example, does not permit an identification of the gemstone to be made, and in the absence of further information, any gemstone producing a green slow phosphorescence marker or an "absence" marker upon UV excitation would need to be "referred" for further testing using an alternate apparatus.

Advantageously, the apparatus of FIGS. 3 to 7 comprises a second measurement location 110b, configured to measure one or more properties of a gemstone. In this embodiment, the second measurement location 110b comprises a photoluminescence (PL) measurement cell.

A gemstone passing through the PL measurement cell on the surface of the rotatable disc 103 undergoes laser excitation at around 450 nm with a 3 mm diameter beam at an angle of 41° from the vertical. Detection of PL is carried out using a miniature spectrometer over a 3 mm diameter measurement area using a single lens system at 0° from the vertical. The position of the gemstone on the rotatable disc 103 is known accurately by the controller 117 and is therefore used to trigger a PL measurement when the gemstone enters the PL measurement cell. The excitation laser, spectrometer and collection optics are optimised to allow a good quality (high signal to noise) PL spectrum to be acquired from moving gemstones within a time frame of approximately 150 milliseconds (the gemstone taking approximately 150 milliseconds to traverse the 3 mm diameter PL measurement area).

Once the PL spectrum has been acquired it is transmitted to the controller 117 and analysed. A determination regarding the gemstone under test is produced and the gemstone is identified, based upon the presence of a Raman line and/or detection of Ni related PL features. The determination may be made based upon the results for the gemstone under test received from both the first and second measurement locations 110a, 110b, and therefore the determination may not be made until a gemstone has passed through both measurement locations 110a, 110b.

The presence in the spectrum of a sharp, single Raman line centred at around 1332 cm$^{-1}$ is an indicator that the gemstone under test contains diamond material and therefore is not a simulant i.e. that the gemstone is not composed of a substance other than diamond. The presence in the spectrum of Ni related PL features at around 787 nm in the absence of a stronger 793 nm feature.is an indicator that the gemstone under test is a natural diamond i.e. not a synthetic diamond. Therefore, the presence of both a sharp, single Raman line at around 1332 cm$^{-1}$ and Ni related PL features at 787 nm but not 793 nm is an indicator that the gemstone under test is a natural diamond. In contrast, the absence of a Raman line at around 1332 cm$^{-1}$ is an indicator that the gemstone under test is non-diamond. The detection algorithm used by the controller 117 reaches a determination before the next gemstone in the separated stream of gemstones enters the PL measurement area.

Therefore, a gemstone which exhibited green slow phosphorescence during testing at the first measurement location 110a, i.e. the luminescence measurement cell, can be identified as either natural diamond or synthetic diamond following testing at the second measurement location 110b, i.e. the PL measurement cell. As discussed above, without this capability, green phosphorescing natural diamond could either be incorrectly classified as synthetic diamond, or else might be "referred" for further testing by a further apparatus, resulting in a higher "referral" rate.

The apparatus 101 of FIGS. 3 to 7 may therefore utilise a combination of different markers detected at the two measurement locations 110a, 110b to identify a gemstone, thus significantly reducing the number of gemstones in a batch which will require further testing by an alternate apparatus in order to be identified. Any gemstones which have still not been reliably identified after passing through both measurement locations 110a, 110b will typically be dispensed into the collection bin 105 designated "refer". Such gemstones can then be subjected to further tests.

Table 1 illustrates how combinations of different markers detected at the two measurement locations 110a, 110b of the apparatus 101 shown in FIGS. 3 to 7 may be used to identify a particular gemstone. The stone can then be dispensed into an appropriate collection bin 105.

Beginning from the left, the contents of the first column of Table 1 (Raman) indicate whether a sharp, single Raman line centred at around 1332 cm$^{-1}$ is present ("1332") or not present ("Not 1332") in the PL spectrum. As discussed above, in this example a PL spectrum is taken at the second measurement location 110b.

The contents of the second and third columns of Table 1 (Phos 1, Phos 2) indicate whether certain of the phosphorescence markers discussed above are present or absent. As discussed above, in this example, phosphorescence is measured at the first measurement location 110a. "Blue" and "Not Blue" in the second column ("Phos 1") indicates the presence and absence respectively of the blue fast phosphorescence marker comprising luminescence in a wavelength band peaking at about 450 nm and a decay time of less than about 80 ms after the end of the associated excitation pulse. The third column ("Phos 2") indicates the presence and colour of slow phosphorescence having a decay time greater than about 80 ms. "Turquoise" in the third column indicates that this slow phosphorescence marker comprises luminescence having a wavelength peaking at about 480 nm and a decay time greater than 80 ms after the end of the associated excitation pulse, as discussed above. "Not Turquoise" in the third column indicates the absence of the turquoise slow phosphorescence marker. It will be appreciated that testing for these two markers comprises testing for phosphorescence in two separate time windows (i.e. <80 ms after the end of the excitation pulse and >80 ms after the end of the excitation pulse).

The contents of the fourth column of Table 1 (Fluorescence) indicate whether the weak green fluorescence marker discussed above, having a wavelength of about 510 nm, is present (Weak Green) or absent (Not Weak Green). Testing for the weak green fluorescence marker may comprise testing in a time window synchronised with an excitation pulse i.e. testing for the marker during excitation of the gemstone. As discussed above, in this example, fluorescence is measured at the first measurement location 110a.

The contents of the fifth column of Table 1 (PL) indicate whether specific Ni related PL features are present (a 787 nm feature in the absence of a stronger 793 nm feature) or not in the PL spectrum. As discussed above, in this example a PL spectrum is taken at the second measurement location 110b.

A dash in any column means that any result is possible and that this measurement should be ignored. For example, as indicated in Row 1 of Table 1, where no sharp, single Raman line centred at around 1332 cm$^{-1}$ is present in the PL spectrum (Not 1332), the gemstone under test can be identified as a simulant (i.e. non-diamond, such as cubic zirconia) regardless of which other markers may or may not be present.

slow phosphorescence marker are both present, but the blue fast phosphorescence marker, the weak green fluorescence marker and the Ni related PL features at 787 nm in the PL spectrum are all absent, the gemstone under test will be dispensed to the "refer" collection bin.

Figure 8:
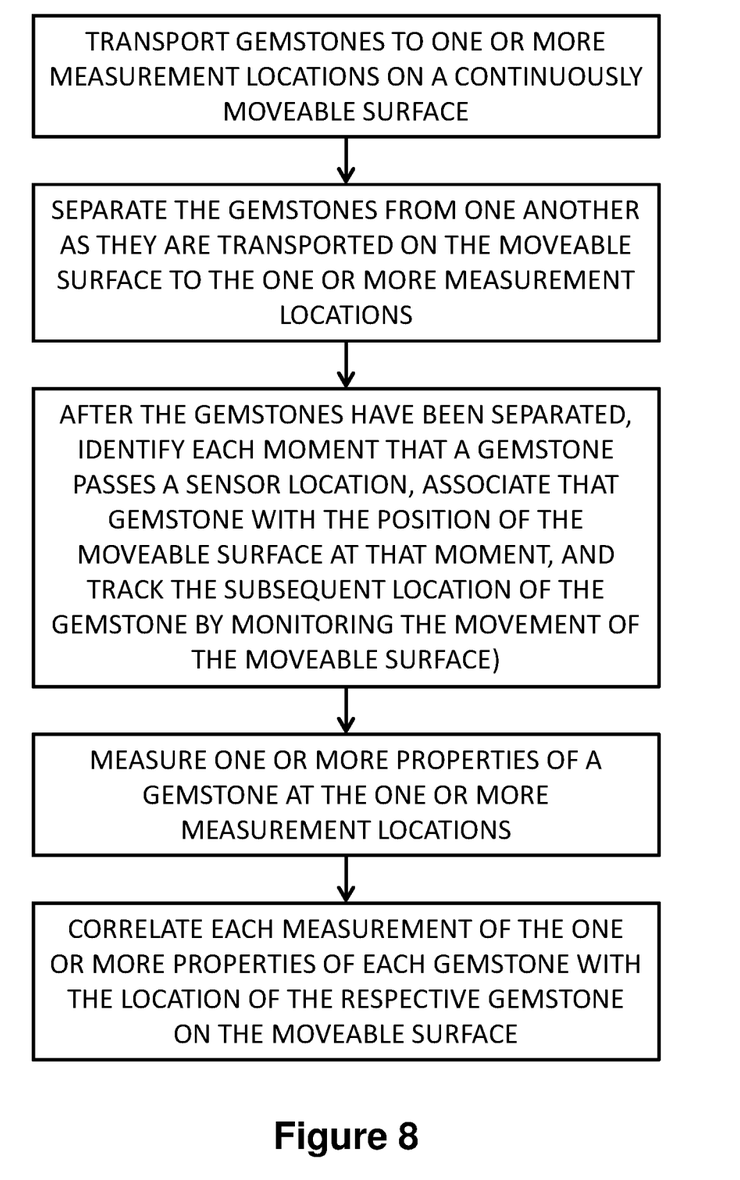
FIG. 8 is a flow chart illustrating a method of sorting gemstones from a batch of gemstones.

With reference to FIG. 8, a method of sorting gemstones from a batch of gemstones comprises the steps of:
Step 1: transporting gemstones to one or more measurement locations on a continuously moveable surface;
Step 2: separating the gemstones from one another as they are transported on the moveable surface to the one or more measurement locations;
Step 3: after the gemstones have been separated, identifying each moment that a gemstone passes a sensor location, associating that gemstone with the position of the moveable surface at that moment, and tracking the subsequent location of the gemstone by monitoring the movement of the moveable surface;
Step 4: measuring one or more properties of a gemstone at the one or more measurement locations; and
Step 5: correlating each measurement of the one or more properties of each gemstone with the location of the respective gemstone on the moveable surface.

It will be appreciated by the person skilled in the art that various modifications may be made to the above described embodiment, without departing from the scope of the present invention. For example, although the embodiment described above comprises two measurement locations 110a, 110b, other embodiments may comprise more than two measurement locations, each measuring one or more properties of a gemstone. Alternatively, measurements of more than one property of a gemstone may be carried out at a single measurement location.

Further, although Table 1 above illustrates testing for phosphorescence markers in two separate time windows, further time windows may be utilised to test for one or more further phosphorescence markers, as discussed above.

Furthermore, it will be appreciated that the markers identified above may be used as indicators of the type of gemstones even if the measurements are acquired using a different instrument.

The invention claimed is:
1. An apparatus for sorting gemstones from a batch of gemstones, the apparatus comprising:
one or more measurement locations, each comprising at least one measurement device configured to measure one or more properties of a gemstone;

TABLE 1

|   | Raman | Phos 1 | Phos 2 | Fluorescence | PL | Identification |
|---|---|---|---|---|---|---|
| 1 | Not 1332 | — | — | — | — | Simulant |
| 2 | 1332 | Blue | — | — | — | Natural |
| 3 | 1332 | Not Blue | Blue | — | — | Natural |
| 4 | 1332 | Not Blue | Turquoise | Weak Green | — | HPHT Synthetic |
| 5 | 1332 | Not Blue | Turquoise | Not Weak Green | 787 nm | Natural |
| 6 | 1332 | Not Blue | Turquoise | Not Weak Green | No 787 nm | Refer |
| 7 | 1332 | Not Blue | Not Turquoise | — | 787 nm | Natural |
| 8 | 1332 | Not Blue | Not Turquoise | — | No 787 nm | Refer |

As can be seen from Table 1, the majority of gemstones will be identified as natural diamond, simulant (i.e. non-diamond), or HPHT synthetic. Only in a few cases will a gemstone be referred for further testing. For example, as shown in Row 6 of Table 1, in the case where the Raman line at around 1332 cm$^{-1}$ in the PL spectrum and the turquoise a continuously moveable surface for supporting the gemstones thereon and for transporting the gemstones to the one or more measurement locations, wherein the moveable surface is a rotatable disc and the gemstones are transported by the rotatable disc through the one or more measurement locations, wherein the one or more measurement locations are at the rotatable disc;
a separation device for separating the gemstones from one another as they are transported on the moveable surface to the one or more measurement locations;
a location trigger comprising a sensor at a sensor location for identifying when the gemstone passes through the sensor location; and
a controller for receiving a signal from the location trigger, recording the position of the moveable surface when the signal is received, and tracking the subsequent location of the gemstone by monitoring the movement of the moveable surface such that a measurement of the one or more properties of each gemstone can be correlated with a location of the respective gemstone on the moveable surface.

2. The apparatus as claimed in claim 1, further comprising an orientation device for orienting the gemstones as they are transported to the separation device, such that the gemstones are oriented into their most stable configuration prior to being separated from one another.

3. The apparatus as claimed in claim 2, wherein the orientation device comprises a pair of opposed parallel vertical walls which form a substantially semi-circular channel, the pair of walls being oscillated by an oscillator such that a central portion of the pair of walls oscillates in a direction generally transverse to a direction of travel of the gemstones.

4. The apparatus as claimed in claim 1, wherein each measurement device is configured to measure the one or more properties of the gemstone as it moves through the measurement location on the moveable surface.

5. The apparatus as claimed in claim 1, wherein the separation device comprises a series of cam surfaces located above and closely proximate to the moveable surface, each cam surface being inclined to a direction of travel of the moveable surface, so that the gemstones are pushed successively further from their initial line of travel by successive cams in the series.

6. The apparatus as claimed in claim 1, wherein the moveable surface has a hard black anodized surface.

7. The apparatus as claimed in claim 1, further comprising a plurality of dispensing locations, each location comprising a collection bin and an associated dispensing mechanism.

8. The apparatus as claimed in claim 7, wherein the associated dispensing mechanism comprises one of a push bar and a spiked foam wheel.

9. The apparatus as claimed in claim 1, comprising two measurement locations.

10. The apparatus as claimed in claim 9, wherein a first measurement location comprises a first measurement device configured to measure luminescence emitted by the gemstones following excitation by a UV source.

11. The apparatus as claimed in claim 10, wherein the first measurement device is configured to measure luminescence in a plurality of different time windows following a pulse of excitation by the UV source.

12. The apparatus as claimed in claim 11, wherein the different time windows include one or more of:
a window synchronised with the start and end of the pulse so as to measure fluorescence;
a window which opens at the end of the pulse and closes after about 80 ms to measure fast phosphorescence; and
a window which opens about 80 ms after the end of the pulse and closes before a subsequent pulse to measure slow phosphorescence.

13. The apparatus as claimed in claim 10, wherein the first measurement device is configured to measure the wavelength of the luminescence.

14. The apparatus as claimed in claim 10, wherein a second measurement location comprises a measurement device configured to measure photoluminescence emitted by the gemstones following laser excitation.

15. The apparatus as claimed in claim 1, further comprising a hopper configured to receive and deliver a batch of gemstones onto a surface of the rotatable disc.

16. The apparatus as claimed in claim 1, wherein gemstones are delivered onto an inner region of the rotatable disc and are subsequently dispensed into a collection bin located adjacent an outermost region of the rotatable disc, according to their measured properties.

17. A method of sorting gemstones from a batch of gemstones, the method comprising the steps of:
transporting gemstones to one or more measurement locations on a continuously moveable surface, wherein the moveable surface is a rotatable disc and the gemstones are transported by the rotatable disc through the one or more measurement locations, wherein the one or more measurement locations are at the rotatable disc;
separating the gemstones from one another as they are transported on the moveable surface to the one or more measurement locations;
after the gemstones have been separated, identifying each moment that a gemstone passes a sensor location, associating that gemstone with the position of the moveable surface at that moment, and tracking the subsequent location of the gemstone by monitoring the movement of the moveable surface;
measuring one or more properties of a gemstone at the one or more measurement locations; and
correlating each measurement of the one or more properties of each gemstone with the location of the respective gemstone on the moveable surface.

18. The method as claimed in claim 17, wherein the one or more properties comprises one or more specific markers in the luminescence and/or photoluminescence properties of the gemstone.

19. The method as claimed in claim 18, wherein one of the one or more specific markers is a blue fast phosphorescence marker comprising luminescence in a wavelength band peaking at about 450 nm and a decay time of less than about 80 ms, and wherein testing for the blue fast phosphorescence marker comprises testing, in a time window opening at or after the end of an excitation pulse and ending about 80 milliseconds after the end of the associated excitation pulse, for a luminescence band peaking at about 450 nm.

20. The method as claimed in claim 18, wherein one of the one or more markers is a turquoise slow phosphorescence marker comprising luminescence having a wavelength peaking at about 480 nm and a decay time greater than 80 milliseconds, and wherein testing for the turquoise slow phosphorescence marker comprises testing, in a time window opening about 80 milliseconds after the end of an associated excitation pulse, for a luminescence band centred around 480 nm, the time window optionally closing about 500 ms after the end of the associated excitation pulse.

21. The method as claimed in claim 18, wherein one of the one or more markers is a weak green fluorescence marker having a wavelength of about 510 nm, and wherein testing for the weak green fluorescence marker may comprise testing in a time window synchronised with an excitation pulse.

22. The method as claimed in claim 18, wherein one of the one or more markers is a single Raman line centred at around 1332 cm$^{-1}$ in a photoluminescence spectrum of the gemstone.

23. The method as claimed in claim 22, comprising identifying a stone as simulant if no 1332 cm$^{-1}$ Raman line is present.

24. The method as claimed in claim 18, comprising identifying a stone as natural diamond if:
- a 1332 cm$^{-1}$ Raman line is present, and
  - a blue fast phosphorescence marker is present; or
  - a blue fast phosphorescence marker is not present and a turquoise slow phosphorescence marker is present and no weak green fluorescence is present and a photoluminescence marker around 787 nm without a stronger line at 793 nm is present; or
  - a blue fast phosphorescence marker is not present and no turquoise slow phosphorescence marker is present and a photoluminescence marker around 787 nm is present.

25. The method as claimed in claim 18, comprising identifying a stone as HPHT synthetic if a 1332 cm$^{-1}$ Raman line is present, a blue fast phosphorescence marker is not present, a turquoise slow phosphorescence marker is present, and a weak green fluorescence is present.

26. The method as claimed in claim 18, comprising referring a stone for further tests if:
- a 1332 cm$^{-1}$ Raman line is present, and
  - a blue fast phosphorescence marker is not present and a turquoise slow phosphorescence marker is present and weak green fluorescence marker is not present and a photoluminescence marker around 787 nm is not present; or
  - a blue fast phosphorescence marker is not present and no turquoise slow phosphorescence marker is present and a photoluminescence marker around 787 nm is not present.

* * * * *